(12) United States Patent
Agostinelli

(10) Patent No.: US 11,774,431 B2
(45) Date of Patent: Oct. 3, 2023

(54) SYSTEM AND METHOD FOR ELECTRICAL AND MAGNETIC MONITORING OF A MATERIAL

(71) Applicant: IDEACURIA INC., Richmond Hill (CA)

(72) Inventor: Gregory A. Agostinelli, Richmond Hill (CA)

(73) Assignee: IDEACURIA INC., Richmond Hill (CA)

( * ) Notice: Subject to any disclaimer, the term of this patent is extended or adjusted under 35 U.S.C. 154(b) by 0 days.

(21) Appl. No.: 17/672,570

(22) Filed: Feb. 15, 2022

(65) Prior Publication Data

US 2022/0221437 A1 Jul. 14, 2022

Related U.S. Application Data

(63) Continuation of application No. 16/990,716, filed on Aug. 11, 2020, now abandoned, which is a
(Continued)

(51) Int. Cl.
*G01N 33/14* (2006.01)
*G06N 20/00* (2019.01)
(Continued)

(52) U.S. Cl.
CPC .......... *G01N 33/14* (2013.01); *G01N 27/023* (2013.01); *G01N 27/028* (2013.01); *G01N 27/07* (2013.01);
(Continued)

(58) Field of Classification Search
CPC .... G01N 27/023; G01N 27/028; G01N 27/72; G01N 27/74; G01N 33/14; G06N 20/00; A23L 35/00
(Continued)

(56) References Cited

U.S. PATENT DOCUMENTS 3,966,973 A 6/1976 Henry et al.
4,045,729 A * 8/1977 Loh .................. G01N 27/70
340/634
(Continued)

OTHER PUBLICATIONS

WIPO, International Search Report and Written Opinion, dated Mar. 6, 2018, re PCT International Patent Application No. PCT/IB2017/057184.
(Continued)

*Primary Examiner* — Robert R Raevis
(74) *Attorney, Agent, or Firm* — Perry + Currier Inc.

(57) ABSTRACT

A system and method for monitoring a characteristic of a material by measuring electrical or magnetic properties of the material. The system includes a material monitoring device having at least one electrode and at least one magnetic coil, and is in communication with a machine learning model trained to recognize characteristics of the material based on electrical and magnetic properties of the material. The material can be stimulated with an electrical stimulus or stimulating magnetic field, and an electrical response signal or magnetic response signal can be measured. Applications to monitoring water quality, beverages, foodstuffs, and other characteristics of materials is discussed.

26 Claims, 9 Drawing Sheets

Related U.S. Application Data continuation of application No. 15/815,014, filed on Nov. 16, 2017, now Pat. No. 10,775,358.

(60) Provisional application No. 62/422,774, filed on Nov. 16, 2016.

(51) Int. Cl.
| | |
|---|---|
| *G01N 27/02* | (2006.01) |
| *G01N 27/07* | (2006.01) |
| *G01N 27/72* | (2006.01) |
| *G01N 27/74* | (2006.01) |
| *A23L 35/00* | (2016.01) |

(52) U.S. Cl.
CPC ............ *G01N 27/72* (2013.01); *G01N 27/74* (2013.01); *G06N 20/00* (2019.01); *A23L 35/00* (2016.08)

(58) Field of Classification Search
USPC ....... 324/345, 346, 217, 218, 438, 204, 228, 324/232–243, 634, 639–641, 643, 324/663–670, 672–689, 692–694, 698, 324/704–717; 361/277, 280, 281; 73/61.41, 1.02, 1.3, 1.06, 19.01, 19.1, 1, 73/23.3, 23.21, 23, 31, 23.34, 73/335.01–335.5, 31.01–31.3, 31.5, 31.06, 73/53.01, 61.42, 61.43
See application file for complete search history.

(56) References Cited

U.S. PATENT DOCUMENTS

| | | |
|---|---|---|
| 6,085,599 A | 7/2000 | Feller |
| 6,677,859 B1 | 1/2004 | Bensen |
| 6,911,822 B2 | 6/2005 | Augustine et al. |
| 6,912,917 B2 | 7/2005 | Brugger et al. |
| 8,259,299 B2 | 9/2012 | Harra et al. |
| 9,482,643 B2 | 11/2016 | Rapoport et al. |
| 9,597,439 B2 | 3/2017 | Jones et al. |
| 2006/0207319 A1 | 9/2006 | Krozer et al. |
| 2007/0106143 A1 | 5/2007 | Flaherty |
| 2007/0166730 A1 | 7/2007 | Menon et al. |
| 2014/0097829 A1 | 4/2014 | Wang et al. |
| 2016/0041292 A1* | 2/2016 | Wahrlich ............... G01V 3/165 324/329 |
| 2016/0067497 A1 | 3/2016 | Levine et al. |
| 2016/0131603 A1 | 5/2016 | Van Der Mei et al. |
| 2016/0366536 A1 | 12/2016 | Agostinelli et al. |
| 2018/0052133 A1* | 2/2018 | Godfrey ............... G01N 27/226 |
| 2018/0325414 A1* | 11/2018 | Marashdeh .......... A61B 5/0033 |

OTHER PUBLICATIONS

WIPO, International Preliminary Report on Patentability, dated May 31, 2019, re PCT International Patent Application No. PCT/IB2017/057184.

USPTO, Non-Final Rejection, dated Dec. 18, 2019 re U.S. Appl. No. 15/815,014

USPTO, Final Rejection, dated May 1, 2020 re U.S. Appl. No. 15/815,014.

USPTO, Notice of Allowance and Fees Due, dated Jun. 4, 2020 re U.S. Appl. No. 15/815,014.

* cited by examiner

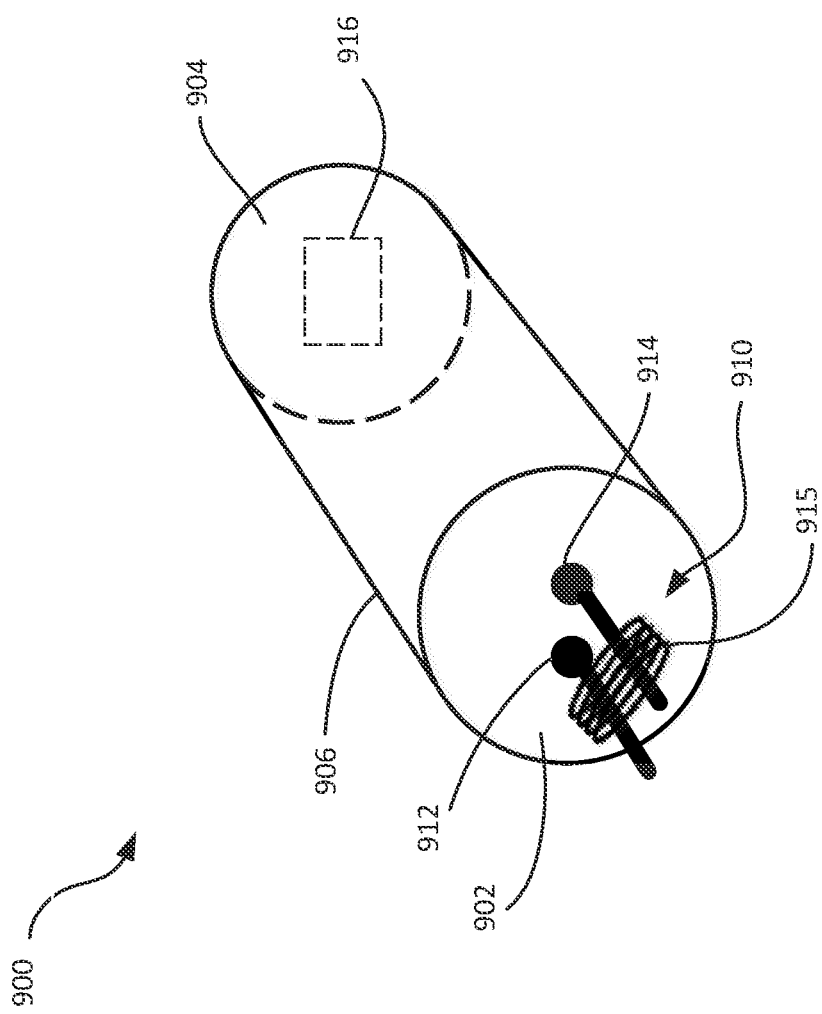

SYSTEM AND METHOD FOR ELECTRICAL AND MAGNETIC MONITORING OF A MATERIAL

CROSS-REFERENCE TO RELATED APPLICATIONS

This application is a continuation application of U.S. patent application Ser. No. 16/990,716, filed on Aug. 11, 2020, which is a continuation of U.S. patent application Ser. No. 15/815,014, filed on Nov. 16, 2017, which claims priority to U.S. 62/422,774, filed Nov. 16, 2016, all of which are incorporated herein by reference.

FIELD

The present disclosure relates generally to material monitoring.

BACKGROUND

There are many materials used today that have characteristics that change over time, have the potential to expire, or may be contaminated. Consumers generally do not have a reliable means of monitoring the current status and characteristics of these products before or after purchasing or delivery. One such class of products is water that can be delivered by plumbing or water bottles. Potential problems with water include contamination, whether in a municipal water distribution system or in a water packaging facility. Another class of such products is beverages, especially wines, which are known to change characteristics over time, including characteristics relevant to taste of the wine. Another class of such products is foodstuffs. A common problem with beverage and foodstuff products is that these products may spoil, decompose, or proceed past their ideal period for consumption, maturity point, or peak flavor point.

For water, a consumer typically relies on municipal water treatment systems or quality control in the water bottle packaging facility. For beverage products and foodstuffs, some manufacturers provide an estimated "best before" date or a date on which the product was produced, which serves as a crude benchmark for estimating when a product has spoiled or passed its ideal consumption point. The typical consumer relying on these dates, however, must trust that the product contained within the packaging is still in good condition upon consumption and that it will match the characteristics advertised by the manufacturer.

Another class of materials that experiences relevant changes in characteristics over time are chemical products. The changes may be induced by environmental factors or they may occur spontaneously. They may be due to physical process changes such as evaporation or on-going chemical reaction processes such as ion exchange or other reactions. A chemical substance may only be useful to the purchaser when it possesses characteristics within a particular range.

Current solutions to monitoring water, beverages, foodstuffs, and similar materials typically involve invasive testing of the product or measurements performed on gas/vapor given off by the product. Many solutions require that the container be opened, thus altering the product's state or in many cases accelerating the spoiling process. Further, solutions that reference the gas/vapor given off by the product are indirect and may have reduced accuracy or may be incapable of measuring the desired characteristics.

SUMMARY

According to an aspect of the disclosure, a system for monitoring a characteristic of a material includes a sensor device, the sensor device including at least one electrode, the at least one electrode configured to contact the material and to apply an electrical stimulus to the material and measure an electrical response signal of the material, and at least one magnetic coil, the at least one magnetic coil configured to apply a stimulating magnetic field to the material and measure a magnetic response signal, a computing device configured to apply machine learning for determining a not directly measurable characteristic of the material based on at least the electrical response signal and the magnetic response signal, wherein at least one of the electrical response signal and the magnetic response signal is influenced by at least one of the electrical stimulus and the stimulating magnetic field altered by the material, and wherein the machine learning applied via a machine learning model trained with library data to recognize the not directly measurable characteristic of the material, the library data relating at least one of a previously measured electrical response signal and a previously measured magnetic response signal to a known not directly measurable characteristic of the material, a circuit connecting the sensor device and computing device, and a body housing the sensor device.

In some embodiments, the electrical stimulus is generated by transmitting an initiating electrical signal to the at least one electrode, and the stimulating magnetic field is generated by transmitting the initiating electrical signal to the at least one magnetic coil.

In some embodiments, the initiating electrical signal includes a varying signal profile.

In some embodiments, at least one of the electrical response signal and the magnetic response signal is transformed into a transformed signal profile, and the machine learning is applied to the transformed signal profile.

In some embodiments, the stimulating magnetic field includes a sinusoidal oscillating signal.

In some embodiments, the at least one electrode includes an input electrode and an output electrode, and the output electrode is configured to apply the electrical stimulus to the material, and the input electrode is configured to measure the electrical response signal.

In some embodiments, the at least one magnetic coil includes an input magnetic coil and an output magnetic coil, and the output magnetic coil is configured to apply the stimulating magnetic field to the material, and the input magnetic coil is configured to measure the magnetic response signal.

In some embodiments, the system further includes a material conduit, the material conduit defining an interior for transporting the material, the body housing the sensor device is attachable to the material conduit, and the at least one electrode of the sensor device extending into the interior of the material conduit.

According to another aspect of the disclosure, a system for monitoring a characteristic of a material includes a sensor device, the sensor device including at least one electrode, the at least one electrode configured to contact the material and to measure an electrical response signal, and at least one magnetic coil, the at least one magnetic coil configured to apply a stimulating magnetic field to the material and to measure a magnetic response signal, a computing device configured to apply machine learning for determining a not directly measurable characteristic of the material based on at least the electrical response signal and the magnetic response signal, wherein at least one of the electrical response signal and the magnetic response signal is influenced by the stimulating magnetic field altered by the material, and wherein the machine learning applied via a machine learning model trained with library data to recognize the not directly measurable characteristic of the material, the library data relating at least one of a previously measured electrical response signal and a previously measured magnetic response signal to a known not directly measurable characteristic of the material, a circuit connecting the sensor device and computing device, and a body housing the sensor device.

In some embodiments, the stimulating magnetic field is generated by transmitting an initiating electrical signal to the at least one magnetic coil, the initiating electrical signal including a varying signal profile.

In some embodiments, the magnetic response signal is transformed into a transformed signal profile, and the machine learning is applied to the transformed signal profile.

In some embodiments, the stimulating magnetic field includes an sinusoidal oscillating signal.

In some embodiments, the at least one magnetic coil includes an input magnetic coil and an output magnetic coil, and wherein the output magnetic coil is configured to apply the stimulating magnetic field to the material, and the input magnetic coil is configured to measure the magnetic response signal.

In some embodiments, the system further includes a material conduit, the material conduit defining an interior for transporting the material, wherein the body housing the sensor device is attachable to the material conduit, the at least one electrode of the sensor device extending into the interior of the material conduit.

According to another aspect of the disclosure, a system for monitoring a characteristic of a material includes a sensor device, the sensor device including at least one electrode, the at least one electrode configured to contact the material and to apply an electrical stimulus to the material, and at least one magnetic coil, the at least one magnetic coil configured to apply a stimulating magnetic field to the material and to measure a magnetic response signal, a computing device configured to apply machine learning for determining a not directly measurable characteristic of the material based on at least the magnetic response signal, wherein the magnetic response signal is influenced by at least one of the electrical stimulus and the stimulating magnetic field altered by the material, and wherein the machine learning applied via a machine learning model trained with library data to recognize the not directly measurable characteristic of the material, the library data relating at least one of a previously measured electrical response signal and a previously measured magnetic response signal to a known not directly measurable characteristic of the material, a circuit connecting the sensor device and computing device; and a body housing the sensor device.

In some embodiments, the electrical stimulus is generated by transmitting an initiating electrical signal to the at least one electrode, and the stimulating magnetic field is generated by transmitting the initiating electrical signal to the at least one magnetic coil, and wherein the initiating electrical signal comprises a varying signal profile.

In some embodiments, the magnetic response signal is transformed into a transformed signal profile, and the machine learning is applied to the transformed signal profile.

In some embodiments, the at least one magnetic coil includes an input magnetic coil and an output magnetic coil, and wherein the output magnetic coil is configured to apply the stimulating magnetic field to the material, and the input magnetic coil is configured to measure the magnetic response signal.

In some embodiments, the system further includes a material conduit, the material conduit defining an interior for transporting the material, the body housing the sensor device is attachable to the material conduit, the at least one electrode of the sensor device extending into the interior of the material conduit.

According to another aspect of the disclosure, a system for monitoring a characteristic of a material includes a sensor device, the sensor device including at least one magnetic coil, the at least one magnetic coil configured to apply a stimulating magnetic field to the material and to measure a magnetic response signal, a computing device configured to apply machine learning for determining a not directly measurable characteristic of the material based on at least the magnetic response signal, wherein at least the magnetic response signal is influenced by the stimulating magnetic field altered by the material, and wherein the machine learning applied via a machine learning model trained with library data to recognize the not directly measurable characteristic of the material, the library data relating at least one of a previously measured magnetic response signal to a known not directly measurable characteristic of the material, a circuit connecting the sensor device and computing device, and a body housing the sensor device.

In some embodiments, the sensor device further includes at least one electrode, the at least one electrode configured to contact the material and to measure an electrical response signal, the computing device is configured to apply machine learning for determining a not directly measurable characteristic of the material based on at least the electrical response signal and the magnetic response signal, at least one of the electrical response signal and the magnetic response signal is influenced by the stimulating magnetic field altered by the material, and the library data relates at least one of a previously measured electrical response signal and a previously measured magnetic response signal to a known not directly measurable characteristic of the material.

Other features and advantages are described below.

BRIEF DESCRIPTION OF THE DRAWINGS

Preferred embodiments of the present disclosure will now be described, by way of example only, with reference to the attached Figures, wherein:

FIG. 9 depicts a perspective view of a device for monitoring characteristics of a material, according to another non-limiting embodiment.

DETAILED DESCRIPTION

Figure 1:
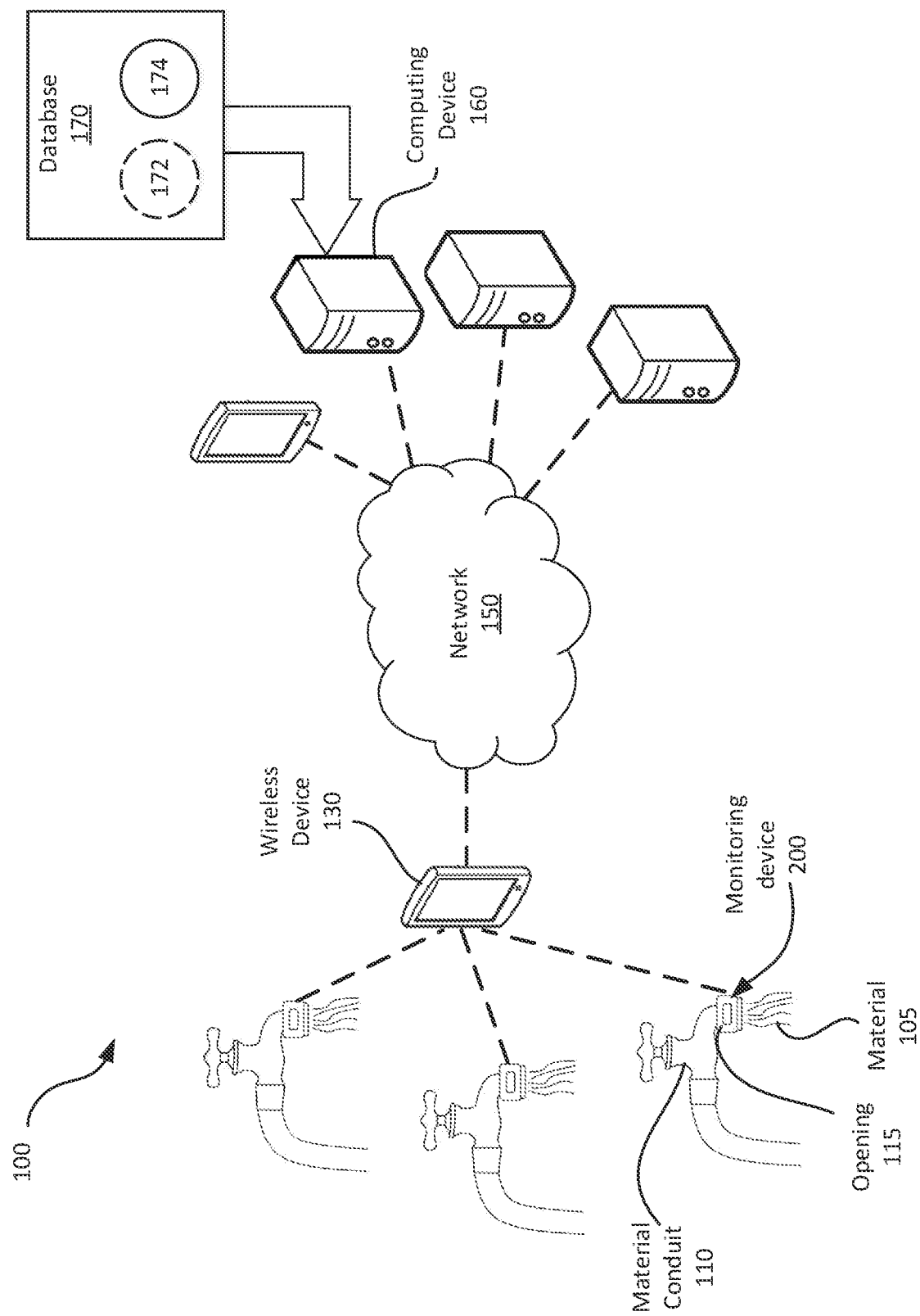
FIG. 1 depicts a schematic diagram of a system for monitoring characteristics of a material, according to a non-limiting embodiment.

The disclosure relates to a system and method for monitoring a characteristic of a material by measuring electrical or magnetic properties of the material. The system includes a material monitoring device having at least one electrode and at least one magnetic coil, and is in communication with a machine learning model trained to recognize characteristics of the material based on electrical and magnetic properties of the material. The material can be stimulated with an electrical stimulus or stimulating magnetic field, and an electrical response signal or magnetic response signal can be measured. This disclosure discusses applications to the monitoring of water quality, beverages, foodstuffs, and other materials.

The system may include a computing device hosting a database and a machine learning model, or may include a cloud computing environment having a distributed database and a machine learning model. The material monitoring device can thereby be made with minimal storage and processing capabilities, with storage and processing duties being handled by an external cloud computing device or cloud computing environment, allowing for efficient energy operation of the material monitoring device.

The material monitoring device can be made sufficiently compact to be able to directly take measurements inside small conduits and vessels containing materials. For example, the material monitoring device may take measurements along a water faucet or water material. As another example, the material monitoring device may be at least partly housed within a cork of a wine bottle and may take measurements from the wine in the wine bottle.

The material monitoring device includes at least one electrode and at least one magnetic coil for measuring electrical and magnetic signals from the material. In some implementations, an electrode may provide an electrical stimulus to the material, or a stimulating magnetic field to the material, to stimulate the electrical or magnetic signal measured from the material. In some implementations, a plurality of electrodes, or a plurality of magnetic coils, may be used, with some electrodes or magnetic coils being dedicated to providing a stimulus, with others being dedicated to measurement. The stimuli and response signals may be incorporated into the machine learning model for training and for determining a characteristic of the material.

Additionally, the material monitoring device can be made with electrodes that can be in direct contact with the material being monitored, improving the electrical connection with the material and thereby the accuracy of any electrical measurement taken, without disturbing the material by requiring the vessel to be opened for inspection. Similarly, the material monitoring device can be made with magnetic coils in proximity to the material being monitored.

A library relating previously measured electrical measurements and magnetic measurements of materials to characteristics of those materials can be developed to train a machine learning model to recognize characteristics of those materials based on electrical or magnetic signal profile measurements of those materials. A machine learning model can thereby be trained to recognized characteristics of a material which are not directly measurable by conventional or practical means. Thus, a machine learning model can be trained to recognize a not directly measurable characteristic of a material. For example, it may not be feasible to conduct sample gathering and laboratory analysis of a home's water supply on a continual basis to determine the presence of a contaminant in the water, and thus such a procedure may be sufficiently lengthy and cumbersome such that the presence of the contaminant is considered not directly measurable. However, by application of the system described herein, a machine learning model may be trained to recognize that measurement of, for example, a particular magnetic signal profile from water flowing through a water faucet, following a particular electrical stimulus, indicates the presence of a contaminant, such as a microbe contaminant, in a home's water supply. A water quality monitoring device installed on the home water faucet may thereby be configured to immediately indicate such contamination. As another example, it may become recognized that the measured electrical impedance of wine may be related to the development of a particular flavor of the wine throughout its aging process. In other examples, a beneficial characteristic of water or other material may be monitored, such as the quantity of a nutrient, a preferable level of mineral, the presence of a beneficial microbe, etc.

Other features and advantages of the system are described more fully below, where non-limiting embodiments of the system are described with reference to the following Figures. For convenience, reference numerals may be repeated (with or without an offset) to indicate analogous components or features.

FIG. 1 shows a system 100 for monitoring a material 105, according to a non-limiting embodiment. The system 100 includes one or more material conduits 110 delivering a material 105. The system 100 includes a material monitoring device 200 attached to a material conduit 110 monitoring the material 105 passing through material conduit 110.

In the present embodiment, the material 105 being monitored comprises tap water passing through a water conduit such as a water pipe or a water faucet. The material monitoring device 200 is located at the opening 115 of the material conduit 110.

The material monitoring device 200 is in communication with a wireless device 130. The wireless device 130 is in communication over network 150 with one or more computing devices 160 storing a database 170. The network 150 can include a wireless cellular data network, a Wi-Fi network, a local-area network, a wide-area network (WAN), a Bluetooth pairing or connection, the internet, a virtual private network (VPN), a combination of such, and similar. The database 170 stores measurement data 172 and library data 174, discussed in greater detail below.

Briefly, the material monitoring device 200 measures electrical and magnetic properties of the material 105 and transmits the results as measurement data 172, which may include other ancillary data, including data related to any electrical or magnetic stimulus, to the wireless device 130.

The wireless device 130 is in communication with the computing device 160 which stores the database 170. Measurement data 172 is periodically transmitted by the material monitoring device 200 to the wireless device 130, which in turn transmits the measurement data 172 to the computing device 160. The library data 174 stores existing data relating one or more electrical properties or magnetic properties of a material 105 to characteristics of the material 105.

The computing device 160 is configured to compute, correlate, or otherwise determine a characteristic of the material 105 by comparing the measured electrical properties or magnetic properties of the material 105 in measured data 172 to library data 174. The computing device 160 can communicate an indication of this characteristic or the characteristic itself to interested parties (not shown), such as a consumer, owner, retailer, or manufacturer across the network 150, whether through the wireless device 130 or otherwise. In some embodiments, an indication that a characteristic has reached a threshold can be transmitted as an alert to the wireless device 130.

Some characteristics, although not measurable directly, can be recognized by a machine learning model incorporating measurement data 172 and library data 174, which relates electrical and magnetic properties of water to known, not directly measurable, characteristics of water. For example, a machine learning model may be trained to recognize that measurement of a particular magnetic signal profile from water flowing through a water faucet, following a particular electrical stimulus, indicates the presence of a contaminant such as a microbe contaminant, a chemical contaminant, a metal contaminant such as lead, a mineral contaminant, or other contaminant in a home's water supply. Thus, where a characteristic is not directly measurable, such as, in the case of a contaminant, where detection of the contaminant may involve a sufficiently lengthy and cumbersome process such that the presence of the contaminant is considered not directly measurable, a machine learning model may be trained to recognize the not directly measurable characteristic with library data 174 relating previously measured electrical or magnetic properties of the material to where the presence of the contaminant is known. Thus, the library data may relate previously measured electrical or magnetic properties to known not directly measurable characteristics of the material. For example, the library data 174 may include magnetic signal profiles which indicate the presence of a particular microbe contaminant, or library data 174 may include electrical signal profiles which indicate a quantity of chemical. In some examples, an electrical or magnetic signal may indicate the presence of a beneficial compound, such as a nutrient, a preferable level of mineral, a beneficial microbe, etc. The machine learning model and signal analysis are discussed in greater detail below with reference to FIG. 5.

In the present embodiment, the wireless device 130 includes a smart phone running an operating system such as, for example, Android®, iOS®, Windows® mobile, BB 10, or similar. The wireless device 130 receives alerts and indications from the computing device 160 regarding characteristics of the material 105, thereby serving as an end-user device for monitoring a material.

In other embodiments, the wireless device 130 includes a tablet computer, a personal digital assistant (PDA), computer, or other machine with communications ability within range of the material monitoring device 200. In these embodiments, the wireless device 130 similarly serves as an end-user device for monitoring a material.

In still other embodiments, the wireless device 130 includes a wireless access point, wireless router, or similar network device. In these embodiments, a computing device 160 serves as an end-user device for monitoring a material.

In still other embodiments, a first computing device 160 is in communication with a second computing device 160, the second computing device 160 serving as an end-user device for monitoring a material.

In the present embodiment, an computing device 160 includes a computing device running a server application with storage, communication, and processing means.

A person skilled in the art upon reading this specification will appreciate that the wireless device 130 and the computing device 160 can each be more generally referred to as external computing devices, and that in certain embodiments the responsibility of each external computing device may be interchangeable. In the present embodiment, measurement data 172 is transmitted from the material monitoring device 200, temporarily stored on the wireless device 130, and transmitted to a computing device 160 for permanent storage on database 170, for computation, and for determination of a characteristic of the material with reference to library data 174. In the present embodiment, cost, size, and energy use of the material monitoring device 200 is reduced by keeping storage and computation away from the material monitoring device 200, and having only measurement and data transmission take place on the material monitoring device 200, with a wireless device 130 acting as an intermediary data transport device.

In other embodiments, these responsibilities can be distributed arbitrarily across the material monitoring device 200, wireless device 130, and computing device 160, or a cloud computing environment. For example, the database 170 comprising library data 174 may be stored on a single wireless device 130, or may be distributed across several wireless devices 130, eliminating the need for a computing device 160. Alternatively, a material monitoring device 200 or a plurality of material monitoring devices 200 may be in direct communication with a computing device 160 or a plurality of computing devices 160, eliminating the need for a wireless device 130. Furthermore, the person skilled in the art upon reading this specification will appreciate that storage, computation, correlation, and machine learning techniques can take place directly on a single or a plurality of material monitoring devices 200, on a single or plurality of wireless devices 130, or on a single or plurality of computing devices 160. In further embodiments, a plurality of material monitoring devices 200 include sufficient storage and communication capability to host a distributed database comprising library data, and sufficient processing capability to determine characteristics of materials and communicate alerts of such characteristics.

It is contemplated that, in some embodiments, the system 100 includes a plurality of material monitoring devices 200 monitoring a plurality of materials 105 at a plurality of material conduits 110, a plurality of material monitoring devices 200 contributing measurement data 172 to library data 174 for contribution to a machine learning model.

In other applications, materials other than water are monitored. For example, it is understood that the materials 105 being monitored can comprise other fluids, liquids, gases, solids, plasmas, beverages, other alcohols, foodstuffs, chemicals, chemicals undergoing chemical reactions, or any other suitable material of interest for which electronic or magnetic monitoring would be feasible. The material 105 may include beer, liquor, another beverage, a chemical, or any other fluid. In such embodiments, the conduit 110 comprises piping, tubing, hose, spout, or any other conduit suitable to transport the fluid.

In still other applications, the material 105 includes a solid foodstuff that is capable of flow through a conduit and is susceptible to electrical measurements from an electrode and magnetic measurements through a magnetic coil. An example of such a solid foodstuff includes granulated sugar. In such embodiments, the conduit 110 includes a conveyer, trough, or any other mechanism suitable to transport the solid. A example of a solid or semi-solid foodstuff is tomato paste. Such a foodstuff may flow through a conduit and may be forced or extruded through a pair of electrodes that perform one or more of the electrical measurements described herein. Further applications include measurement of gas/vapor. Other examples include medical vaccine monitoring, medication monitoring, or medication authentication.

Figure 2:
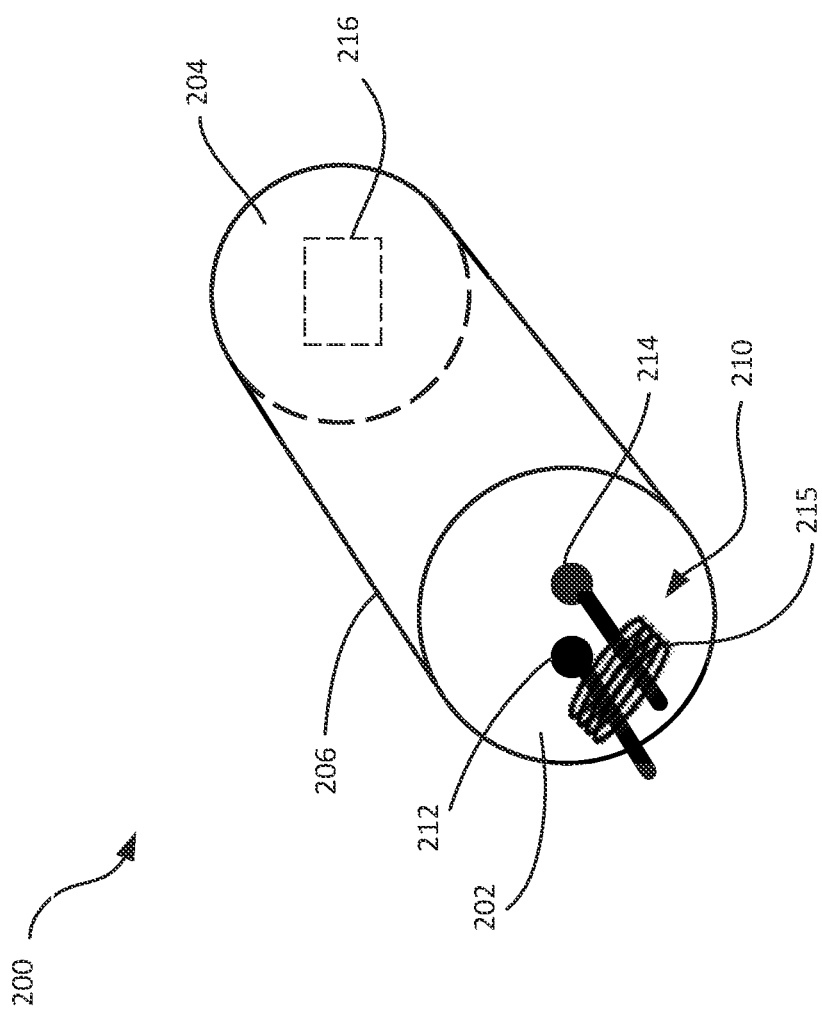
FIG. 2 depicts a perspective view of a device for monitoring characteristics of a material, according to a non-limiting embodiment.

FIG. 2 depicts a perspective view of a material monitoring device 200, according to a non-limiting embodiment. The material monitoring device 200 comprises a body 206 having an interior end 202 and an exterior end 204, a sensor device 210 at the interior end 202, and an exterior indicator 216 at the exterior end 204. With reference to the embodiment in FIG. 1, the material monitoring device 200 can be incorporated into an attachment to an opening of a water faucet, with sensor device 210 oriented toward the material 105 in a manner permitting interaction of the sensor device 210 with the material 105, and the exterior indicator 216 oriented to be visible to a user of the water faucet.

The sensor device 210 comprises an output electrode 212, an input electrode 214, and a magnetic coil 215. The output electrode 212 and input electrode 214 extend into the material 105. The output electrode 212 is used to apply an electrical stimulus to the material 105. In turn, the input electrode 214 is used to measure an electrical response signal of the material 105. The input electrode 214 thus includes a return-path electrode for completing the electrical connection allowing an electrical response signal to return from the material 105.

The magnetic coil 215 is used to apply a stimulating magnetic field to the material 105, and is also used to measure a magnetic response signal from the material 105.

The output electrode 212 and input electrode 214 may include any suitable material for electrical conductivity, including gold, a gold-plated metal, platinum, a platinum-plated metal, carbon, graphite, graphene, silver, silver chloride, silicon, germanium, tin, iron, copper, or brass, or other suitable materials. Similarly, the magnetic coil may include an electromagnet of any suitable material for generating a magnetic field.

The exterior indicator 216 includes at least one of: a simple single color light-emitting diode (LED), a multicolor LED, a moving coil galvanometer, voltmeter or current meter, a piezoelectric transducer, a speaker, a buzzer, a siren, a relay switch, an optical bar graph, a counter such as a numerical counter or any suitable counter, liquid crystal display (LCD), or any other suitable indicator device that interfaces with the circuitry of the material monitoring device 200, as described in greater detail below.

In the present embodiment of a system for monitoring characteristics of water passing through a water faucet, the exterior indicator 216 comprises a two color LED, where the color red indicates the water contains a contaminant, and the green colour indicates that no contaminants are detected.

Although in the embodiment of FIG. 1, the material monitoring device 200 is attached to opening 115 of conduit 110, it is contemplated that the material monitoring device 200 may be located elsewhere along conduit 110, for example, along the piping leading to the water faucet.

In some applications for monitoring liquids, the output electrode 212 and input electrode 214 need not extend into the liquid, but rather conducts measurements on the gas/vapor in the headspace above the liquid to infer properties of the liquid.

Although in the present embodiment shown in FIG. 2, the sensor device 210 is shown having an input electrode and an output electrode, it is contemplated that a single electrode may serve as both input and output electrode. Furthermore, it is contemplated that the sensor device 210 may include an input magnetic coil and an output magnetic coil. A purpose of sensor magnetic coil 43 is to magnetically couple with the product being monitored and optionally allow it to magnetically stimulate the product being monitored and/or optionally measure a magnetic field result from the product being monitored. Moreover, it is contemplated that the sensor device 210 may include a plurality of electrodes, some of the electrodes operating as input electrodes and some as output electrodes, and that the sensor device 210 may include a plurality of magnetic coils, some of the magnetic coils operating as input magnetic coils and some as output magnetic coils.

Various further embodiments of the material monitoring device 200 are contemplated. In one embodiment, the sensor device 210 includes a third electrode. In such an embodiment, the three electrodes are a working electrode, a reference electrode, and a counter electrode, thus enabling additional electro-analytical techniques. For example, the sensor device 210 includes a three-electrode potentiostat system for measuring redox reactions or other types of reactions.

In a further embodiment, the sensor device 210 includes only a single electrode for taking measurements without applying any electrical stimulus to the material 105. In such an embodiment, the sensor device 210 comprises no output electrode, but only a single input electrode for taking input measurements.

Similarly, in a further embodiment, the magnetic coil 215 may be configured for taking magnetic measurements without applying a stimulating magnetic field to the material 105.

In further variations of the material monitoring device 200, the exterior indicator 216 may be omitted. In this variation, the status or characteristics of the material 105 may be communicated to and presented at wireless device 130 or computing device 160.

Figure 3:
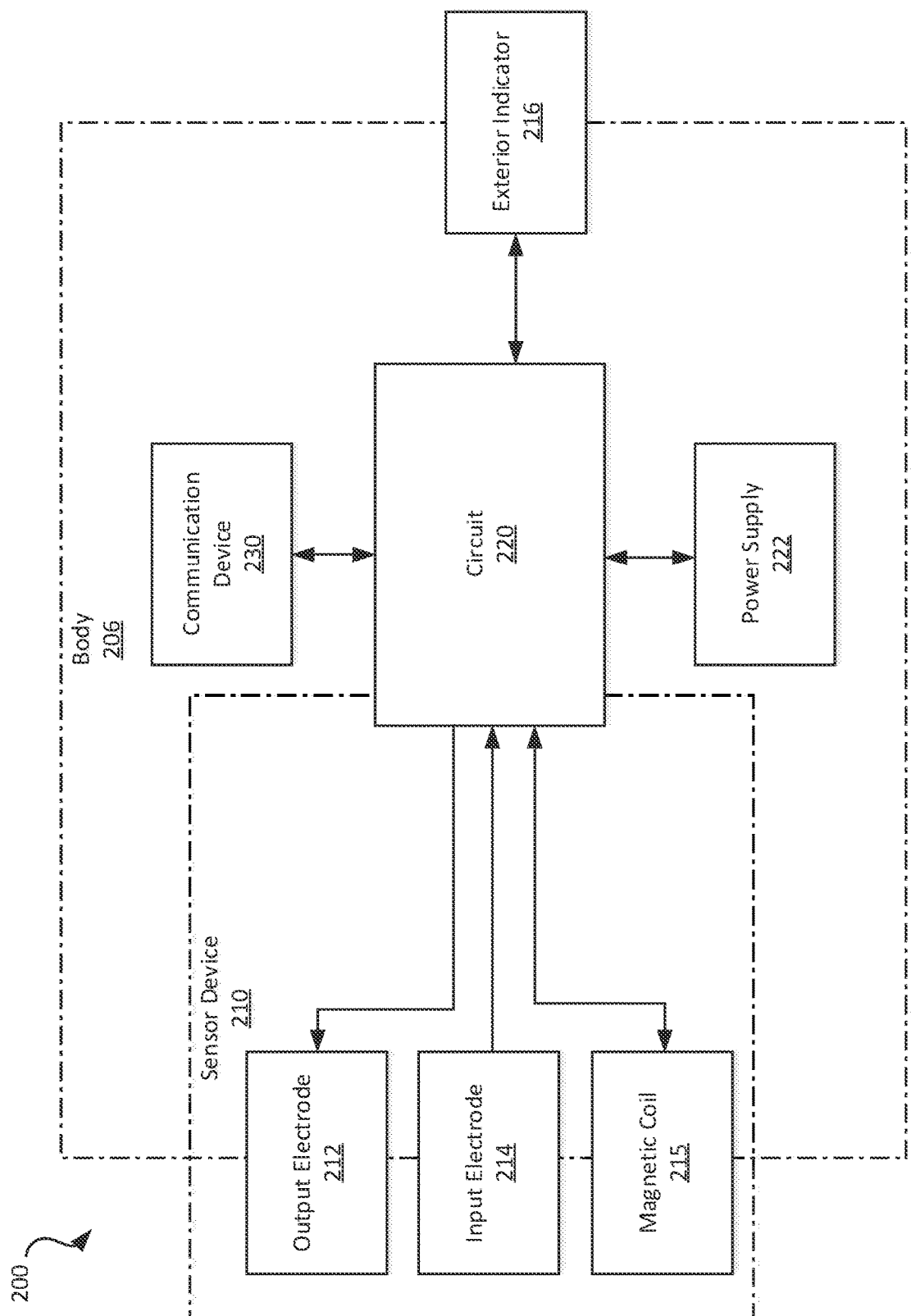
FIG. 3 depicts a functional block diagram of the device of FIG. 2.

FIG. 3 depicts functional blocks of the material monitoring device 200, according to a non-limiting embodiment. The material monitoring device 200 comprises a sensor device 210 comprising an output electrode 212 an input electrode 214, and a magnetic coil 215. The material monitoring device 200 further comprises an exterior indicator 216, a communication device 230, power supply 222, and circuit 220.

The communication device 230 is configured to transmit data corresponding to measured electrical and magnetic properties of the material 105 to the wireless device 130 and/or computing device 160, as the case may be. The communication device 230 comprises a communications antenna, or any other suitable communication device configurable to communicate directly with a wireless device 130 or computing device 160.

The power supply 222 supplies power to the components of the material monitoring device 200. In the present embodiment, the power supply 222 comprises a power harvesting circuit. The power harvesting circuit harvests electrical power from a communications field or by, in the case of a material travelling through a conduit, by kinetic power harvesting from the motion of the material 105. In other embodiments, the power supply 222 comprises a battery, a solar cell, or external power supply connection, such as an AC or DC connection. Although in the present embodiment the power supply 222 is illustrated as being housed within the body 206 of the material monitoring device 200, in other embodiments it is contemplated that the power supply could be exterior to the body 206.

The circuit 220 comprises circuitry for providing electrical connections between the sensor device 210, communication device 230, power supply 222, and exterior indicator 216. In various embodiments, a portion of the circuit 220 forms part of the sensor device 210. Furthermore, in some embodiments, the circuit 220 includes one or more of the following: integrated circuit device power harvesting circuit 52, integrated circuit device communications radio circuit 54, integrated circuit device control state-machine circuit 56, integrated circuit device sensor output stimulator circuit 58, integrated circuit device sensor input measurement circuit 60, and integrated circuit device sensor magnetic stimulation and measurement circuit 61, a processor, a microcontroller, a state machine, a logic gate array, an application-specific integrated circuit (ASIC), a system-on-a-chip (SOC), a field-programmable gate array (FPGA), or similar, capable of executing, whether by software, hardware, firmware, or a combination of such, a method for monitoring characteristics of a material as discussed in greater detail below. In the present embodiment, the circuit 220 implements a system-on-a-chip (SOC). In some embodiments, the circuit 220 includes memory, where measurement data 172 is to be stored on the material monitoring device 200, before, or in addition to, being transmitted to the wireless device 130 or computing device 160.

In various embodiments, the circuit 220 is a discrete electrical circuit made up of separate discrete electrical components. In other embodiments, the circuit 220 includes an ASIC, an FPGA, an SOC, or combinations thereof. Embodiments of the circuit 220 that include a combination of separate discrete electrical components and an ASIC, FPGA, and/or SOC are also contemplated. In various embodiments, portions of the circuit 220 that describe a logical state-machine are implemented as software and/or firmware that operate on a processor or microcontroller. In various embodiments, the circuit 220 further includes an electrode interface portion that includes circuit elements specific to the electrodes for performing electrical stimulation and electrical measurements, and such circuit elements can be considered to be part of the sensor device 210.

In some embodiments, the material monitoring device 200 is configured to conduct electrical measurements of the material 105. In such embodiments, the material monitoring device 200 may conduct impedance spectroscopy, also known as dielectric spectroscopy, for electrically stimulating the material 105 and performing a measurement on the material 105. It is to be understood, however, that in other embodiments, other electro-analytical methodologies can be performed, such as potentiometry, coulometry, voltammetry, square wave voltammetry, stair-case voltammetry, cyclic voltammetry, alternating current voltammetry, amperometry, pulsed amperometry, galvanometry, and polarography, and other suitable electro-analytical methodologies. In various embodiments, several of the aforementioned methodologies are used in combination.

In some embodiments, the material monitoring device 200 further comprises a sensor capable of taking additional measurements, such as acceleration, position, temperature, pressure, color, light intensity, light phase, density, surface tension, viscosity, resistance, impedance, voltage, current, charge, quantity of mass, quantity and direction of force, quantum mechanical properties, or any other suitable property that can be measured by a sensor. In yet other embodiments, the sensor includes a gyroscope or magnetometer.

In some embodiments, the material monitoring device 200 comprises a sensor with a digital interface designed to perform similar measurements, with the sensor interfacing with the circuit 220 through methods such as Two Wire Interface (TWI or I2C compatible), SPI interface, Microwire, 1-Wire, Single Wire Protocol (SWP), or any other suitable digital or analog communications methodologies.

The circuit 220 may control operations of the material monitoring device 200, including initializing the circuit 220 with required startup parameters, initiating and recording measurements of the sensor device 210, packetizing the measurement data 172 into data packets, controlling the communication device 230 for the reception and transmission of data, commands, and ancillary information, any firmware or software updates, and any other suitable information being transmitted or received.

Figure 4:
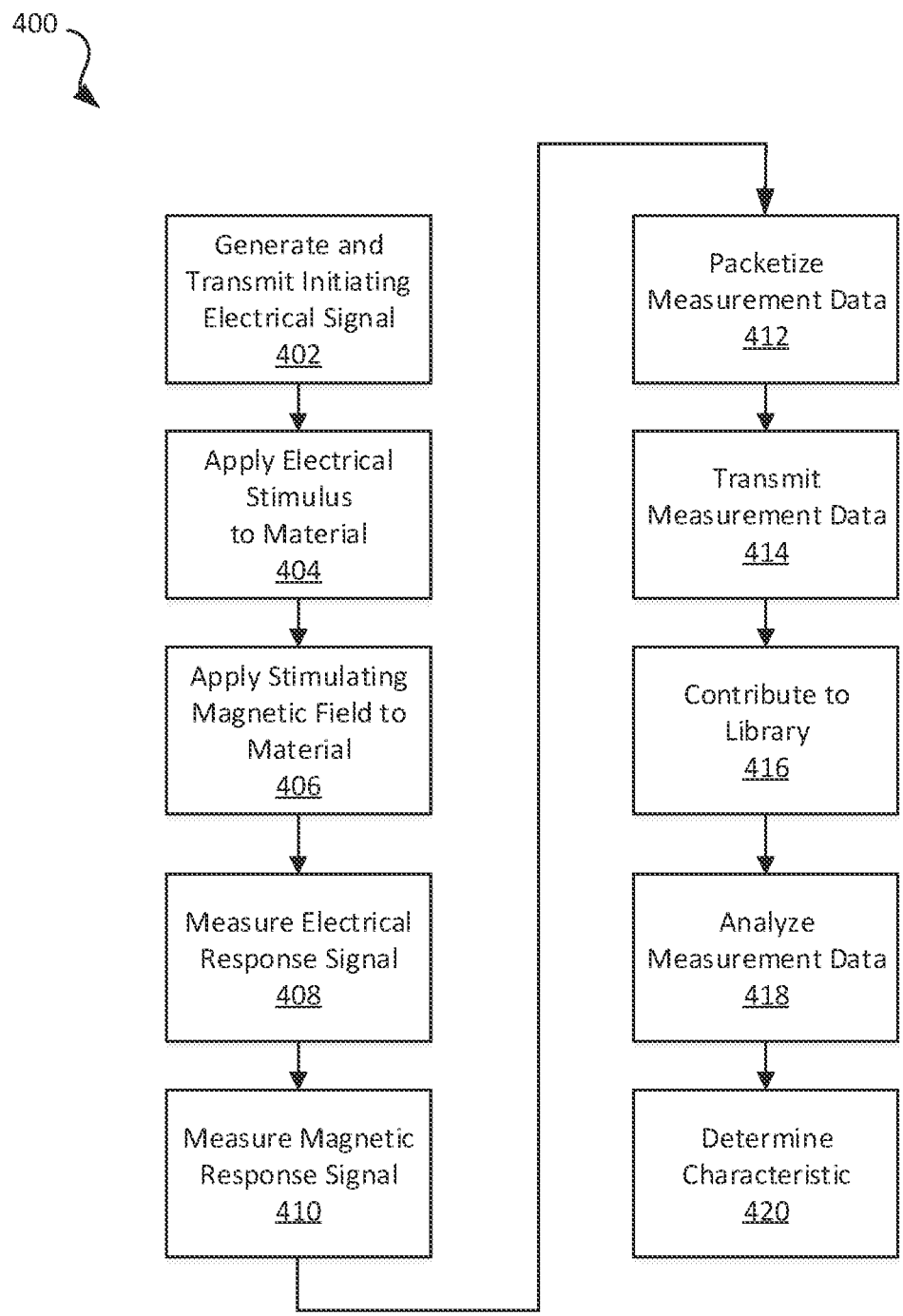
FIG. 4 depicts a flowchart of a method for determining a characteristic of a material, according to a non-limiting embodiment.

FIG. 4 depicts a flowchart of a method 400 for determining a characteristic of a material, according to a non-limiting embodiment. The method 400 is one way in which the characteristics of a material can be monitored. It is to be emphasized, however, that the blocks of method 400 need not be performed in the exact sequence as shown. The method 400 is described as performed by a system and device discussed herein, but this is not limiting and the method can alternatively be performed by other systems and/or devices.

Figure 5:
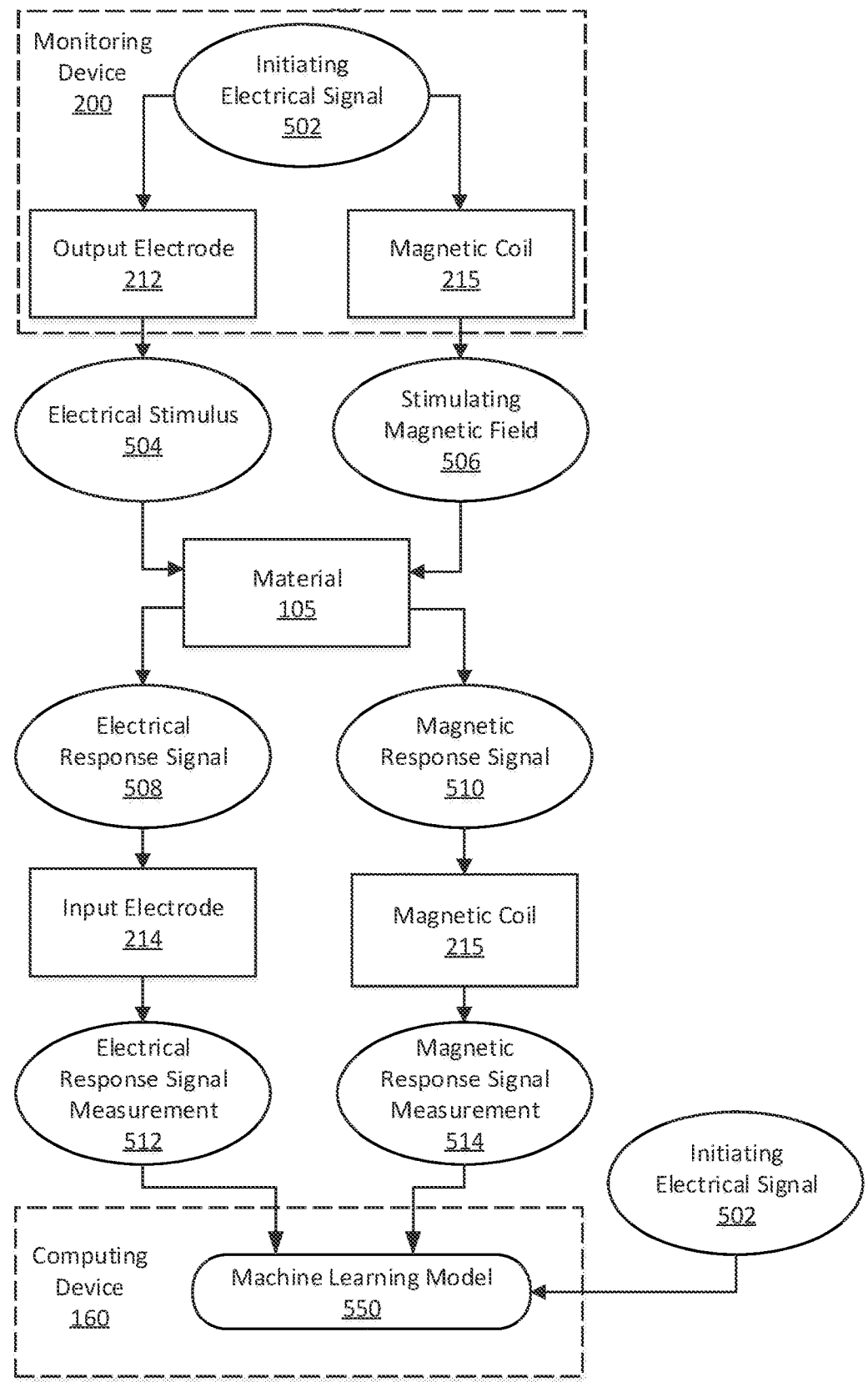
FIG. 5 depicts a schematic diagram of the generation and measurement of electrical and magnetic signals for use in a machine learning model.

With reference to FIG. 5, and with continued reference to FIG. 4, the generation and measurement of electrical and magnetic signals, as described in method 400, are diagrammed schematically.

At block 402, an initiating electrical signal 502 is generated and transmitted. In the present embodiment, the initiating electrical signal 502 is generated on the material monitoring device 200, and is transmitted to the output electrode 212 and magnetic coil 215 on the material monitoring device 200. Transmission of the initiating electrical signal 502 to the output electrode 212 generates an electrical stimulus 504. Transmission of the initiating electrical signal 502 to the magnetic coil 215 generates a stimulating magnetic field 506.

It is to be understood that in other embodiments, the two or more initiating electrical signals 502 may be generated, one for transmission to output electrode 212, another for transmission to the magnetic coil 215. Furthermore, it is to be understood that the initiating electrical signal 502 may be generated elsewhere in system 100, such as from a computing device 160, and transmitted to material monitoring device 200.

The electrical stimulus 504 may be referred to as an electrical electrode stimulation signal profile (EESSP). In some embodiments, the EESSP may comprise a varying signal profile developed to excite the material 105. Such varying signals may include a continuous, discrete, periodic, or an aperiodic signal, or combinations thereof.

In some embodiments, the EESSP may comprise a dynamic AC signal or a static DC signal. In embodiments in which the EESSP comprises a dynamic AC signal, the EESSP may include a sinusoidal oscillating signal. The sinusoidal oscillating signal may be continuous and periodic for a duration sufficient to stimulate the material 105 such that an electrical response signal 508 may be measured. The EESSP may be varied in amplitude, frequency, or other properties. In some embodiments, the EESSP may be generated from a voltage source. In other embodiments, the EESSP may be generated from a current source.

The stimulating magnetic field 506 may be referred to as a magnetic coil stimulation signal profile (MCSSP). In some embodiments, the MCSSP may comprise a varying signal developed to excite the material 105. Such varying signals may include a continuous, discrete, periodic, or aperiodic signal, or combinations thereof.

In some embodiments, the MCSSP may comprise a dynamic AC signal or a static DC signal. In embodiments in which the MCSSP comprises a dynamic AC signal, the MCSSP may include a sinusoidal oscillating signal. The sinusoidal oscillating signal may be continuous and periodic for a duration sufficient to stimulate the material 105 such that a magnetic response signal 510 may be measured. The MCSSP may be varied in amplitude, frequency, or other properties. In some embodiments, the MCSSP may be generated from a voltage source. In other embodiments, the MCSSP may be generated from a current source.

In some embodiments, the MCSSP may comprise a uniform magnetic field.

At block 404, the electrical stimulus 504 is applied to material 105 by output electrode 212.

At block 406, the stimulating magnetic field 506 is applied to material 105 by magnetic coil 215.

At block 408, an electrical response signal 508, detected from material 105, is measured by input electrode 214 as electrical response signal measurement 512. The electrical response signal 508 and thus the electrical response signal measurement 512 is influenced by the electrical stimulus 504 being altered by the material 105. The electrical response signal 508 or electrical response signal measurement 512 may be referred to as an electrical electrode receiving signal profile (EERSP). In some embodiments, the EERSP may be analyzed further in its raw form. In some embodiments, the EERSP may be processed with a mathematical transform for further use in further analysis. The mathematical transforms that may be applied to the EERSP include Fourier transform, Fast Fourier Transform (FFT), Discrete Fourier Transform (DFT), Laplace transform, Z transform, Hilbert transform, Discrete Cosine transform, wavelet transform, discrete wavelet transform, Infinite Impulse Response (IIR), Finite Impulse Response (FIR), or their discrete or accelerated variants, or other mathematical transforms. The mathematical transform can be made in any possible domain such, as but not limited to, time and space domain, frequency domain, Z-plane analysis (Z-domain), and Wavelet analysis, and any such relevant domain or analysis methodology.

At block 410, a magnetic response signal 510, detected from material 105, is measured by magnetic coil 215 as magnetic response signal measurement 514. The magnetic response signal 510 and thus the magnetic response signal measurement 514 is influenced by the stimulating magnetic field 506 being altered by the material 105. The magnetic response signal 510 or magnetic response signal measurement 514 may be referred to as a magnetic coil receiving signal profile (MCRSP). In some embodiments, the MCRSP may be analyzed further in its raw form. In some embodiments, the MCRSP may be processed with a mathematical transform for further use in further analysis. The mathematical transforms that may be applied to the MCRSP include Fourier transform, Fast Fourier Transform (FFT), Discrete Fourier Transform (DFT), Laplace transform, Z transform, Hilbert transform, Discrete Cosine transform, wavelet transform, discrete wavelet transform, Infinite Impulse Response (IIR), Finite Impulse Response (FIR), or their discrete or accelerated variants, or other mathematical transforms. The mathematical transform can be made in any possible domain such, as but not limited to, time and space domain, frequency domain, Z-plane analysis (Z-domain), and Wavelet analysis, and any such relevant domain or analysis methodology.

In some embodiments, the material monitoring device 200 conducts measurements at regular intervals, as some applications require a delay time in order to perform a suitable measurement. In one such embodiment, the wireless device 130 sends instructions to material monitoring device 200 to conduct a measurement at an interval. In another such embodiment, the computing device 160 sends instructions to material monitoring device 200 to conduct a measurement at an interval.

In some embodiments, the electrical response signal 508 and the magnetic response signal 510 are included in measurement data 172. In some embodiments, initiating electrical signal 502 is included in measurement data 172.

At block 412, the measurement data 172 is packetized for transmission to an external computing device. In embodiments in which the circuit 220 comprises memory, the measurement data 172 is recorded on memory before transmission.

At block 414, measurement data 172 is transmitted by the communication device 230 to the wireless device 130, which in turn transmits the measurement data 172 to the computing device 160, which stores the measurement data 172 on database 170.

At block 416, the measurement data 172 transmitted at block 340 is contributed to the library data 174 in database 170. In other embodiments in which the measurement data 172 is not contributed to the library data 174, this block is omitted.

At block 418, measurement data 172 is analyzed at the computing device 160. In the present embodiment, measurement data 172 is analyzed by machine learning model 550.

Although in the present embodiment, the machine learning model 550 is located at the computing device 160, it is emphasized that machine learning, and any analysis at block 418, can take place at a wireless device 130, the material monitoring device 200, or a computing device 160, or can be arbitrarily distributed across monitoring devices 200, wireless devices 130, and computing devices 160, or a cloud computing environment.

At block 420, a characteristic of the material 105 is determined based on the analysis at block 418.

Where a machine learning model 550 is applied in the analysis of measurement data 172 at block 418, several machine learning techniques may be applied. In one such embodiment, a neural network algorithm that employs a Bayesian algorithm and a decision tree analysis to classify the measurement data 172 and report the classified result in order to classify the characteristics of the material 105.

In another embodiment, principal component analysis (PCA) is used on the measurement data 172 to report on the status of the material 105 and also classify its characteristics.

In another embodiment, principal component regression (PCR) is used on the measurement data 172 to report on the status of the material 105 and also classify its characteristics.

In other embodiments, other suitable data analysis techniques may be used, such as clustering analysis, correlation, neural network machine learning algorithms, support vector machine algorithms, random forest algorithms, convolution neural network algorithms, deep belief networks, deep QA networks, or other appropriate algorithms. Machine learning algorithms may include supervised machine learning algorithms or unsupervised machine learning algorithms.

It is to be emphasized that the material monitoring device includes at least one electrode and at least one magnetic coil for measuring electrical and magnetic signals from the material. In some embodiments, an electrical stimulus 504 is applied without a stimulating magnetic field 506, where an electrical response signal 508 may be measured alone, a magnetic response signal 510 may be measured alone, or both an electrical response signal 508 and magnetic response signal 510 may be measured. In some embodiments, a stimulating magnetic field 506 is applied without an electrical stimulus 504, where an electrical response signal 508 may be measured alone, a magnetic response signal 510 may be measured alone, or both an electrical response signal 508 and magnetic response signal 510 may be measured. In some embodiments, both an electrical stimulus 504 and a stimulating magnetic field 506 are applied, simultaneously or sequentially in any scheme, where an electrical response signal 508 may be measured alone, a magnetic response signal 510 may be measured alone, or both an electrical response signal 508 and magnetic response signal 510 may be measured. In some embodiments, a plurality of electrodes, or a plurality of magnetic coils, may be used, with some electrodes or magnetic coils being dedicated to providing a stimulus, with others being dedicated to measurement. In still other embodiments, no electrical stimulus 504 is applied, and no stimulating magnetic field 506 is applied, where an electrical signal alone, a magnetic signal alone, or both, are measured.

Furthermore, it is emphasized some of the blocks of method 400 need not be performed in the exact sequence as shown. For example, the stimulus application in blocks 404 and 406 may be executed simultaneously and the measurement in blocks 408 and 410 may be executed simultaneously.

Furthermore, blocks of the method 400 may thus be omitted or repeated. For example, where the material monitoring device 200 comprises a single electrode, blocks 404 and 408 are replaced with a block at which a measurement is taken.

Although in the present embodiment, machine learning techniques are applied at block 418, other forms of analysis may be used. For example, a polynomial regression may be used on the measurement data 172 to report on the status of the material 105 and also classify its characteristics. Linear regression and non-linear regression may also be used.

In some embodiments, the material monitoring device 200 may vary the electrical stimulus 504 (EESSP) or the stimulating magnetic field 506 (MCSSP) over time. In some embodiments, the EESSP and MCSSP may be varied simultaneously. In some embodiments, the EESSP or MCSSP may be varied independently. The EESSP or MCSSP may be varied through a spectrum of any property of interest. For example, the EESSP may be varied through a band of amplitude, while the MCSSP is varied through a band of amplitude. Any combination of variation of EESSP or MCSSP in any dimension, together or independently, are contemplated. A robust dataset of electrical response signals 508 (EERSP) and magnetic response signals 510 (MCRSP) can thus be gathered for inclusion into and analysis by the machine learning model 550 for determination of a particular family of materials having particular characteristics.

Thus, by application of method 400, a characteristic of a material 105 being monitored is determined with reference to the electrical properties or the magnetic properties of the material 105. These characteristics, although not measurable directly, are recognized by a machine learning algorithm incorporating measurement data 172 and library data 174, which relates electrical properties and magnetic properties of a material to known characteristics of the material. By application of method 400, the library data 174 is expanded with additional data relating electrical properties and magnetic properties of materials to characteristics of materials.

Figure 6:
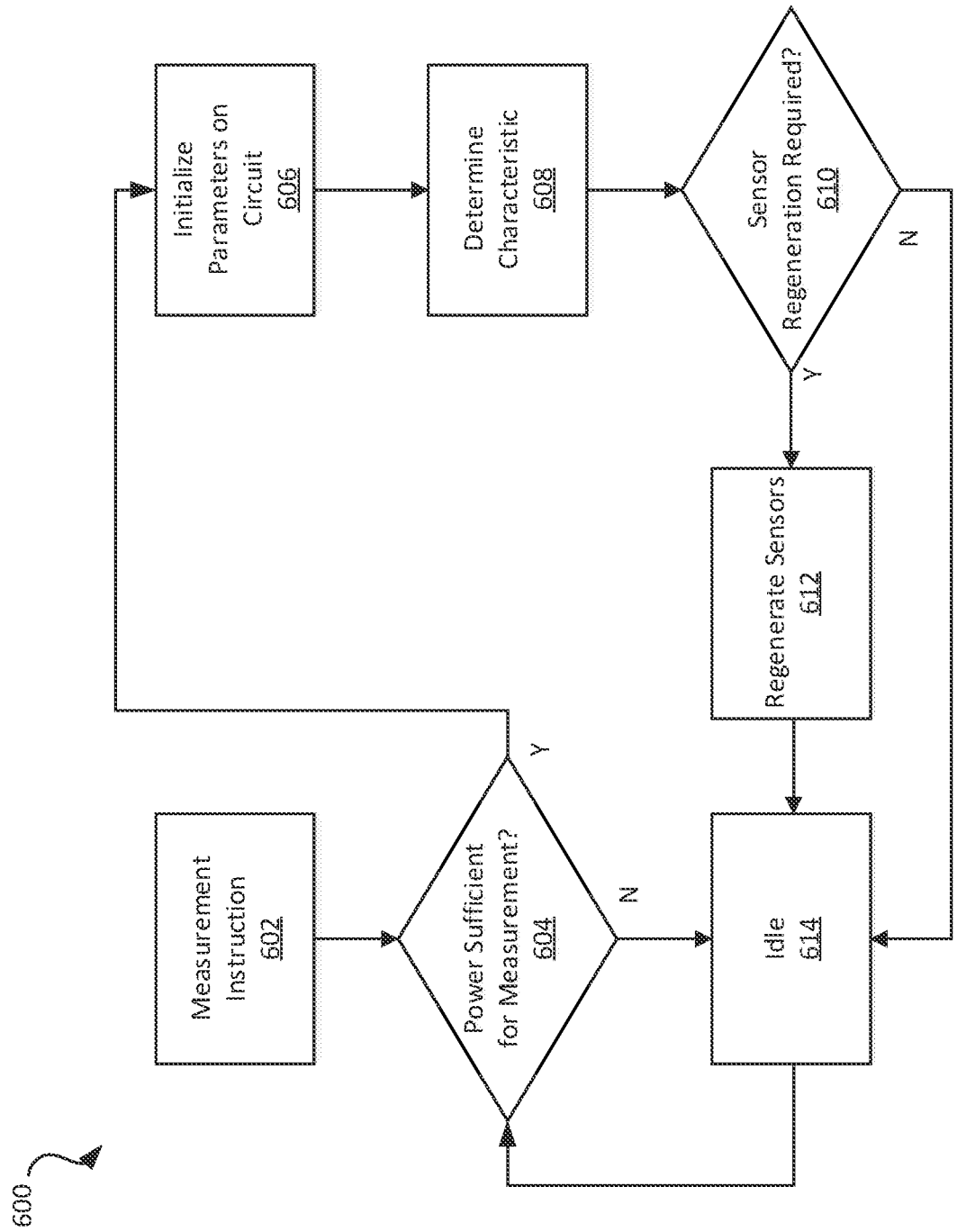
FIG. 6 depicts a flowchart of a method for initializing a device for monitoring characteristics of a material, according to a non-limiting embodiment.

FIG. 6 depicts a flowchart of a method 600 for initializing a material monitoring device 200, according to a non-limiting embodiment. The method 600 is one way in which a material monitoring device can be initialized. It is to be emphasized, however, that the blocks of method 600 need not be performed in the exact sequence as shown. The method 600 is described as performed by a system and device discussed herein, but this is not limiting and the method can alternatively be performed by other systems and/or devices.

In the present embodiment, the material monitoring device 200 remains in an idle state with low energy consumption between conducting measurements. When instructed to conduct a measurement, the material monitoring device 200 undergoes a process of initialization to prepare to conduct a measurement. Upon concluding conducting a measurement, the material monitoring device 200 returns to an idle state.

At block 602, an instruction to conduct a measurement is received by the communication device 230 from an external computing device such as the wireless device 130 or computing device 160.

At block 604, it is determined whether the material monitoring device 200 has sufficient electrical power to conduct a measurement. If sufficient power is present, block 606 is executed. If sufficient power is not present, block 614 is executed. Whether sufficient electrical power is present may be determined by whether a suitable electrical connection is established with an outside power source, whether sufficient battery power is remaining, or whether the energy harvesting circuit has harvested sufficient power for operation.

At block 606, circuit parameters are initialized. For example, initialization includes initializing one or more parameters such as: processor or system clock frequency, analog circuit gain, analog circuit drive strength, analog circuit termination impedance, stimulation values, delay values, filter settings, and any other suitable programmable setting in the device. The aforementioned list of parameters is non-limiting and other parameters are contemplated.

At block 608, a characteristic of material 105 is determined as described with respect to method 400 in FIG. 4 above.

At block 610, it is determined whether sensor regeneration is required. If sensor regeneration is required, block 612 is executed. If sensor regeneration is not required, block 614 is executed. Some sensors require a special regeneration cycle, and others do not, as will be apparent to the person skilled in the art upon reading this specification. For example, a three-electrode potentiostat measurement system that uses very sensitive electrodes may require a regeneration cycle to free ions from the electrode that may collect on the electrode during the measurement cycle.

At block 614, the material monitoring device 200 is in an idle state with low energy consumption. In the present embodiment where the power supply 222 is a power harvesting circuit, the material monitoring device 200 waits until sufficient power is harvested for a measurement to be conducted.

It will be understood by the person skilled in the art upon reading this specification that it is possible to add or omit blocks as necessary to execute any given measurement algorithm.

Figure 7:
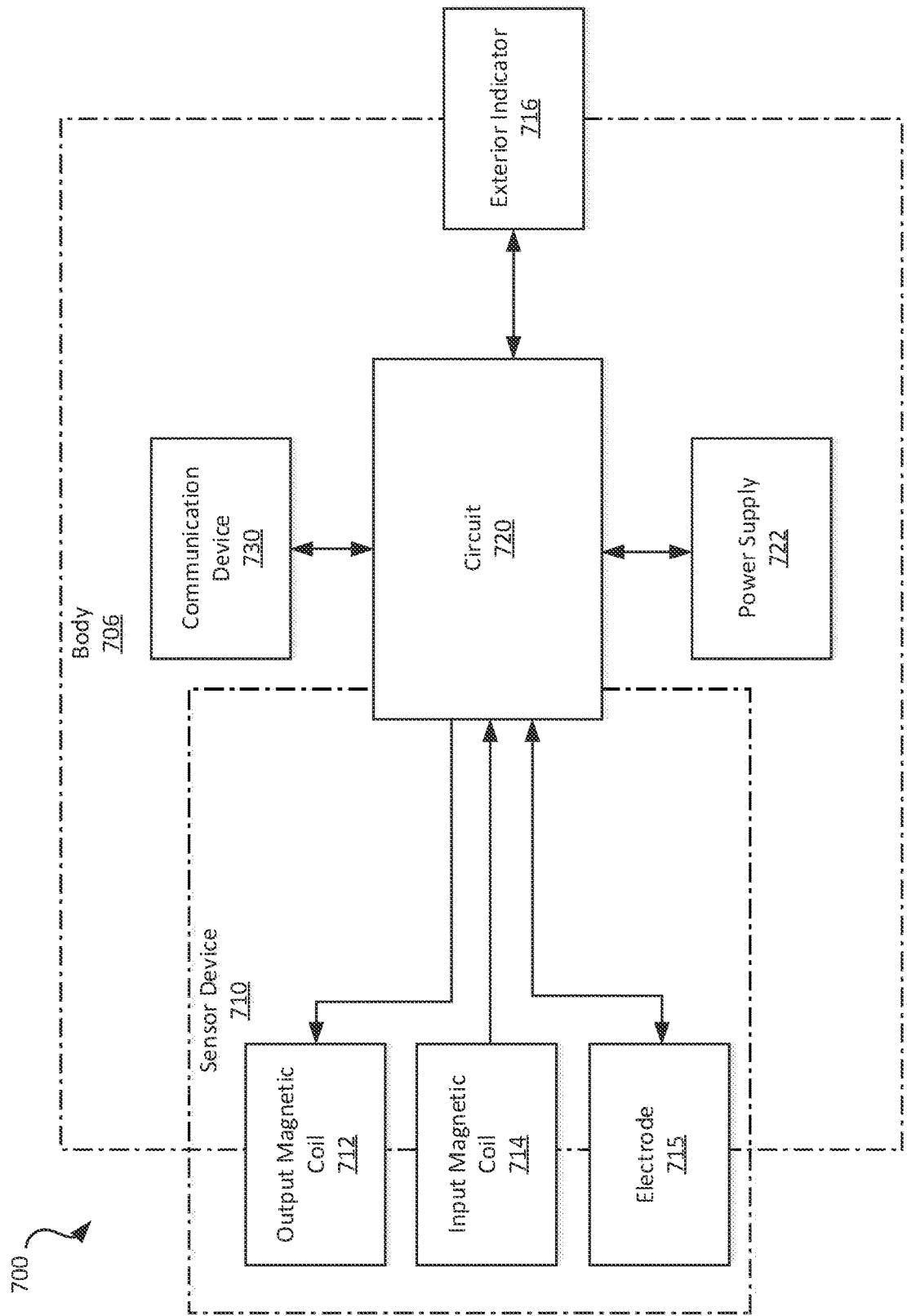
FIG. 7 depicts a functional block diagram of a device for monitoring characteristics of a material, according to another non-limiting embodiment.

FIG. 7 depicts functional blocks of a material monitoring device 700, according to a non-limiting embodiment. The material monitoring device 700 includes a sensor device 710 having an output magnetic coil 712, an input magnetic coil 714, and an electrode 715. The output magnetic coil 712 is generates and applies a stimulating magnetic field to a material 105, and the input magnetic coil 714 is dedicating to measuring a magnetic response signal. The electrode 715 operates to both apply an electrical stimulus to the material 105 and measure an electrical response signal.

With regard to the body 706, communication device 730, circuit 720, power supply 722, and exterior indicator 716, reference may be had to the description of analogous components in FIG. 3.

Figure 8:
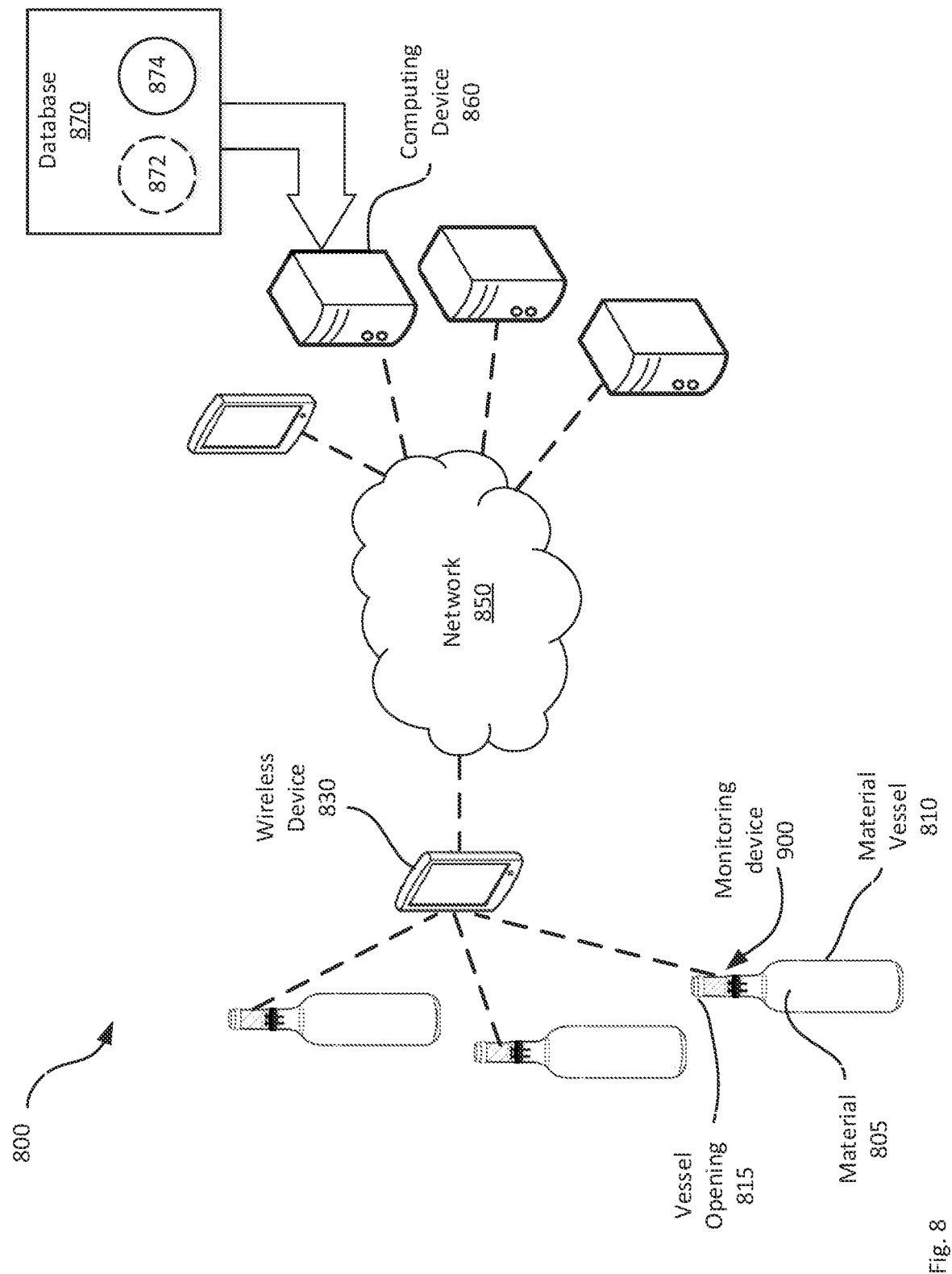
FIG. 8 depicts a schematic diagram of a system for monitoring characteristics of a material, according to another non-limiting embodiment.

FIG. 8 shows a system 800 for monitoring a material 805, according to a non-limiting embodiment. System 800 includes one or more material vessels 810 having vessel openings 815 and containing a material 805. In the present embodiment, the material 805 comprises wine, and the material vessel 810 comprises a wine bottle. System 800 includes a wireless device 830, network 850, computing devices 860, database 870, measurement data 872, and library data 874, for which reference may be had to the description of analogous components in FIG. 1 and the disclosure above.

FIG. 9 depicts a perspective view of the material monitoring device 900, according to a non-limiting embodiment. Material monitoring device 900 includes a body 906, an interior end 902, an exterior end 904, a sensor device 910 having an output electrode 912, an input electrode 914, a magnetic coil 915, and an external indicator, for which reference may be had to the description of analogous components in FIG. 2 and the disclosure above.

The material monitoring device 900 can be incorporated into a wine cork plugging the vessel opening 815 of material vessel 810. The body 906 can be sized to plug the opening 815 of the material vessel 810. In the present embodiment for monitoring wine in a wine bottle, the body 906 comprises a wine bottle cork sized to plug the opening 815 of the wine bottle. However, in other embodiments, the body 906 comprises a barrel bung, a cap, a lid, or an attachment embedded into the side of a vessel, or any other stopper, or means for housing a material monitoring device 900 with a sensor device 910 for measurement of the material 805 being monitored. The material of the body 906 comprises any material suitable for the particular application, such as plastic, natural cork, synthetic cork, agglomerated cork, or wax for the wine bottle application.

In the present embodiment of a system for monitoring characteristics of wine in a wine bottle, when disposed within the opening of a wine bottle, the interior end 902 of the material monitoring device 900 is oriented toward the wine, with the sensor device 910 protruding from the interior end 902, and with output electrode 912 and input electrode 914 extending into the wine contained within the wine bottle.

A sensor device of material monitoring device 900 may thereby measure electrical or magnetic properties of the material 805, and may have electrodes in direct contact with the material 805, or in contact with the gas/vapor in the headspace above the liquid to infer properties of the material 805, as discussed above throughout this disclosure.

An advantage of housing the material monitoring device 900 within a wine bottle cork is that the wine bottle need not be opened, and thus disturbed, in order to inspect the wine for a characteristic. Further, in the present embodiment of monitoring the characteristics of wine, the system 800 could be used to monitor whether the wine is within the optimal taste window or outside of the optimal taste window.

In the present embodiment of a system for monitoring characteristics of wine in a wine bottle, the external indicator 916 comprises a three color LED, where the color red indicates the wine has passed its optimal point of consumption, the color yellow indicates the wine approaching the end of its optimal point of consumption, and the green colour indicates that the wine is within its optimal point of consumption.

In some embodiments, canonical correlation is used on the measurement data 872 to report on the status of the material 805, including, in the case of monitoring the characteristics of wine, whether the wine is within the wine's optimal taste window or approaching its expiry point, and an estimate of how much time may be left before the wine is expected to reach its expiry point.

Although the present example discusses an application to monitoring wine in a wine bottle, wine in a wine bottle is merely one example. Implementations are not limited to monitoring a particular class of materials, whether the material is a fluid, liquid, gas, solid, beverage, foodstuff, chemical, and the vessel is not limited to a particular class of vessel. In addition, other types of containers and delivery conduits instead of vessels are contemplated, such as cartons, packages, kegs, water pipes, water bottles, water containers (e.g., office-style water coolers), to name a few.

In other embodiments, materials other than wine are monitored. For example, it is understood that the materials 805 being monitored can comprise fluids, liquids, gases, solids, plasmas, beverages, other alcohols, foodstuffs, chemicals, chemicals undergoing chemical reactions, or any other suitable material of interest for which electronic monitoring would be feasible. Other examples include medical vaccine monitoring, medication monitoring, or medication authentication. Furthermore, the material vessels 810 includes wine bottles, wine barrels, bottles or barrels of other alcohols, casks, or beverage containers of any kind which can fit a material monitoring device 900.

In other embodiments, wine undergoing a fermentation process in a barrel is monitored via a material monitoring device 900 embedded within the bung of the barrel, or in another suitable location, for indicating the level of completion of the fermentation cycle. Additionally, the aging process of wine can be monitored, with an alert being sent to the wireless device 830 to indicate that the wine has completed its aging process and it is ready to ship to market. Additional characteristics of wine that could be monitored, whether in a bottle or aging in a barrel, include sweetness of flavor, acidity, tannin, fruitiness of flavor, body, aroma, or any other suitable characteristic of wine that is usually measured. These characteristics, although not measurable directly, can be inferred from comparing measurement data 872 to library data 874, which relates electrical properties of wines to known characteristics of wines.

It should be apparent from the above that characteristics of a material can be monitored via the electrical and magnetic properties of the material by a low-power, compact, material monitoring device capable of direct yet non-invasive contact with a material, locatable at a conduit or a vessel, in cooperation with a machine learning model for determining a characteristic of a material using an evolving model based on machine learning techniques.

Characteristics of a material may also be monitored by periodically taking measurements of the material using dedicated sensor devices, such as a pH sensor, temperature sensor, humidity sensor, and the like, and correlating such measurements to a related characteristic of the material in known ways. For example, the it may be known that the pH of tap water may be related to its mineral content, and thus a determination of the mineral content of a sample of water may be made with reference to its pH. However, such monitoring techniques are limited in that they rely on known relationships between a measurement and a characteristic. In contrast, by taking measurements of a material that is not known to relate to a particular characteristic, e.g. by taking measurements related to electrical or magnetic properties of a material, which provides a broader dataset for analysis than a dedicated sensor device, it may be determined that a particular feature of an electrical signal profile, or a particular feature of a magnetic signal profile, relates to a characteristic of the material that is not directly measurable, and relates in a manner which may not have been previously known, or which may not be expressible in the form of a known relationship, such as how the pH level of water is known to be impacted by its mineral content. Further, by considering the connections between electrical properties of a material and magnetic properties of the material, a richer dataset for analysis is provided. For example, electrical stimulation of the material may have a measurable effect on the magnetic properties of the material, which can be recognized by a machine learning model to indicate a particular characteristic that would not otherwise be directly measurable. Thus, a more expansive system for monitoring the characteristics of a material is provided.

The scope of the claims should not be limited by the embodiments set forth in the above examples, but should be given the broadest interpretation consistent with the description as a whole.

The invention claimed is:

1. A communications device for monitoring a characteristic of a material, the communications device comprising:
   a sensor device, the sensor device comprising at least one electrode configured to provide an electrical stimulus to the material and at least one magnetic coil configured to provide a magnetic stimulus to the material, the sensor device configured to measure at least one or more signals responsive to at least one or more of:
      the electrical stimulus, and
      the magnetic stimulus,
   the signal relating to an electrical property of the material;
   an integrated circuit electrically connected to the sensor device, the integrated circuit to communicate measurement data related to the at least one signal to at least one processor via a network, wherein the at least one processor is configured to apply machine learning for determining a not directly measurable characteristic of the material based on the measurement data received from the integrated circuit, the machine learning applied via a machine learning model trained with library data to recognize the not directly measurable characteristic of the material, the library data relating previously measured signals relating the electrical property of the material to known not directly measurable characteristics of the material, and
   a power source to power the sensor device and the integrated circuit; and
   a body containing the sensor device and the integrated circuit, the body positionable with respect to the material to position one of the at least one electrode and the at least one magnetic coil to interact with the material.

2. The communications device of claim 1, wherein the signal is further related to a magnetic property of the material.

3. The communications device of claim 1, wherein the body is attachable to a material conduit for transporting the material, the body comprising:
   the at least one electrode of the sensor device extending into an interior of the material conduit; and
   the at least one magnetic coil positioned to magnetically couple with the material.

4. The communications device of claim 1, wherein the body comprises a stopper configured to plug an opening of a vessel, the vessel defining an interior for containing the material, wherein the stopper is configured to position one of the at least one electrode and the at least one magnetic coil,
   wherein when the stopper is configured to position the electrode, the electrode extends into an interior of the vessel, and
   wherein when the stopper is configured to position the at least one magnetic coil, the magnetic coil magnetically couples with the material.

5. The communications device of claim 4, wherein the vessel comprises a wine bottle, the material comprises wine, and the stopper comprises a wine bottle cork.

6. The communications device of claim 1, wherein the power source is selected from a group consisting of: a power harvesting circuit, a battery, a solar cell, and an alternating current electrical power adapter.

7. The communications device of claim 1, wherein one or more of the sensor device, the integrated circuit, and the at least one processor are configured to perform an analytical methodology selected from a group consisting of: potentiometry, coulometry, voltammetry, impedance spectroscopy, square wave voltammetry, stair-case voltammetry, cyclic voltammetry, alternating current voltammetry, amperometry, pulsed amperometry, galvanometry, and polarography.

8. The communications device of claim 1, wherein the material is selected from a group consisting of: a fluid, a liquid, a gas, a vapor, a plasma, and a solid.

9. A method of chemical monitoring, vaccine monitoring, medication monitoring, medication authentication, wine monitoring, foodstuffs monitoring, water monitoring, or monitoring of chemicals undergoing a chemical reaction utilizing the communications device of claim 1.

10. The communications device of claim 1 configured to use a signal to drive the magnetic coil to produce a stimulus, wherein the signal is one of a static signal and a dynamic signal.

11. The communications device of claim 10 wherein the signal is a dynamic signal selected from a list consisting of: a sine wave, a square wave, a series of pulses, a complex signal that repeats a pattern, and a complex signal that does not repeat a pattern.

12. The communications device of claim 1 further comprising one of a display device and an audio device connected to the integrated circuit to output an indication of the not directly measurable characteristic of the material.

13. The use of the communications device of claim 1 configured to communicate over a network, wherein the network is in communication with one or more of a wireless network and a cloud computing environment.

14. The communications device of claim 1 configured to communicate with a wireless device.

15. The communications device of claim 1, wherein the sensor device further comprises a sensor for measuring a quantum mechanical property.

16. A non-transitory machine-readable medium comprising instructions that when executed cause at least one processor of a computing device to:
   apply machine learning to determine a not directly measurable characteristic of a material based on at least one signal associated with an electrical property of the material;
   wherein the signal associated with the electrical property of the material is measured by at least one electrode in response to a stimulus provided by the at least one electrode or a magnetic coil, wherein measurement data related to the at least one signal is transmitted to the at least one processor via a network from an integrated circuit connected to the at least one electrode and the at least one magnetic coil and housed within a body which houses the at least one electrode and the at least one magnetic coil; and wherein the machine learning is applied via a machine learning model trained with library data to recognize the not directly measurable characteristic of the material, the library data relating previously measured signals associated with the at least one electrical property of the material to known not directly measurable characteristics of the material.

17. The non-transitory machine-readable medium of claim 16 further comprising instructions that when executed cause the at least one processor to apply machine learning to determine the not directly measurable characteristic of the material based on a signal associated with a magnetic property of the material;

wherein the signal associated with the magnetic property of the material is measured by the magnetic coil in response to the stimulus; and wherein the library data further relates to previously measured signals associated with the magnetic property of the material to the known not directly measurable characteristics of the material.

18. A method of chemical monitoring, vaccine monitoring, medication monitoring, medication authentication, wine monitoring, foodstuffs monitoring, water monitoring, or monitoring of chemicals undergoing a chemical reaction utilizing the non-transitory machine-readable storage medium of claim 16.

19. The non-transitory machine-readable storage medium of claim 16, wherein the at least one electrode and the at least one magnetic coil is configured to interact with the material.

20. The non-transitory machine-readable storage medium of claim 16 further comprising instructions that when executed cause the at least one processor to control an external indicator to display data representing the not directly measurable characteristic of the material recognized by the machine learning model, the external indicator is one of a display device and an audio device.

21. The non-transitory machine-readable storage medium of claim 16 further comprising instructions that when executed cause the at least one processor to communicate with one or more of a wireless network and a cloud computing environment.

22. The non-transitory machine-readable storage medium of claim 16 further comprising instructions that when executed cause the at least one processor to control a power supply, the power supply comprising one of a power harvesting circuit and a battery.

23. The non-transitory machine-readable storage medium of claim 16, wherein the computing device comprises a wireless device.

24. The non-transitory machine-readable storage medium of claim 16 further comprising instructions that when executed cause the at least one processor to apply machine learning to determine a not directly measurable characteristic of a material based on at least one signal associated with a quantum mechanical property of the material.

25. A communications system for monitoring a characteristic of a material, the system comprising:
a communications device comprising:
a sensor device comprising an electrode to provide an electrical stimulus to a material and a magnetic coil to provide a magnetic stimulus to a material and to measure a signal responsive to at least one of the electrical stimulus and the magnetic stimulus, the signal associated with an electrical property of the material;
an integrated circuit electrically connected to the sensor device, the integrated circuit to transmit measurement data related to the signal via a network;
a power source to power the sensor device and the integrated circuit; and
a body containing the sensor device and the integrated circuit, the body positionable with respect to the material to position the electrode and the magnetic coil to interact with the material; and
at least one processor to communicate with the communications device via the network, the at least one processor configured to apply machine learning for determining a not directly measurable characteristic of the material based on the measurement data received from the integrated circuit, the machine learning applied via a machine learning model trained with library data to recognize the not directly measurable characteristic of the material, wherein the library data relates previously measured signals associated with the at least one electrical property of the material to known not directly measurable characteristics of the material.

26. The communications system of claim 25 wherein the signal is further related to a magnetic property of the material, and wherein the library data further relates previously measured signals associated with the magnetic property of the material to the known not directly measurable characteristics of the material.

* * * * *